United States Patent [19]

Davidson

[11] Patent Number: 4,581,176

[45] Date of Patent: Apr. 8, 1986

[54] PROCESS FOR PREPARING ALPHA-ARYLACRYLONITRILES

[75] Inventor: Robert I. Davidson, Baton Rouge, La.

[73] Assignee: Ethyl Corporation, Richmond, Va.

[21] Appl. No.: 735,146

[22] Filed: May 17, 1985

[51] Int. Cl.$^4$ .................. C07C 121/75; C07C 121/70; C07C 120/00
[52] U.S. Cl. .................................... 558/341; 558/345
[58] Field of Search ............ 260/465 F, 465 G, 465 K

[56] References Cited

U.S. PATENT DOCUMENTS 4,536,343  8/1985  Ramachandran ............... 260/465 F

OTHER PUBLICATIONS

Jacobs et al., J. Org. Chem., vol. 48, pp. 5134–5135, (1983).

Primary Examiner—Dolph H. Torrence
Attorney, Agent, or Firm—Donald L. Johnson; John F. Sieberth; Patricia J. Hogan

[57] ABSTRACT

An alpha-arylacrylonitrile is prepared by reacting an aryl ketone having a removable hydrogen alpha to the carbonyl group with a cyanide ion source which is free of radicals that would stabilize a cyanohydrin corresponding to the aryl ketone and with a Lewis acid in the presence of an activating amount of water and/or HCl and preferably in the presence of a solvent. In a preferred embodiment, the aryl ketone is a tetralone, the cyanide ion source is sodium cyanide, the Lewis acid is aluminum chloride, and the product is a 1-cyano-3,4-dihydronaphthalene.

19 Claims, No Drawings

PROCESS FOR PREPARING ALPHA-ARYLACRYLONITRILES

FIELD OF INVENTION

This invention relates to alpha-arylacrylonitriles and more particularly to a process for preparing them.

BACKGROUND

It is known that alpha-arylacrylonitriles are useful as chemical intermediates and that they can be prepared in various ways. For example, Jacobs et al., Journal of Organic Chemistry, 1983, Vol. 48, pp. 5134–5135, teach that 6-methoxy-1-cyano-3,4-dihydronaphthalene is useful as an intermediate in the synthesis of steroids and that it can be prepared by (1) the addition of diethylaluminum cyanide to 6-methoxytetralone followed by dehydration or (2) the addition of cyanotrimethylsilane to 6-methoxytetralone followed by treatment with phosphoryl chloride in pyridine. As taught by Jacobs et al., the former method of synthesizing their alpha-arylacrylonitrile is impractical for large scale operations, and the latter method requires two steps.

Copending application Ser. No. 676,479, filed Nov. 29, 1984, now U.S. Pat. No. 4,536,343, in the name of V. Ramachandran, teaches that alpha-arylacrylonitriles can be prepared by reacting an aryl ketone having a removable hydrogen alpha to the carbonyl group with an alkali metal cyanide and aluminum chloride. Copending application Ser. No. 724,474, filed April 18, 1985, in the names of Ramachandran, Davidson, and Maloney teaches that 6-alkoxy-1-cyano-3,4-dihydronaphthalenes can be prepared by reacting a 6-alkoxytetralone with a cyanide ion source which is free of radicals that would stabilize a cyanohydrin corresponding to the 6-alkoxytetralone and with a Lewis acid, optionally in the presence of a small amount of water and/or concentrated HCl.

SUMMARY OF INVENTION

An object of this invention is to provide a novel process for preparing alpha-arylacrylonitriles.

Another object is to provide such a process which is suitable for large scale operations and produces the alpha-arylacrylonitriles from aryl ketones in a single step.

These and other objects are attained by reacting an aryl ketone having a removable hydrogen alpha to the carbonyl group with a cyanide ion source which is free of radicals that would stabilize a cyanohydrin corresponding to the aryl ketone and with a Lewis acid in the presence of an activating amount of water and/or HCl.

DETAILED DESCRIPTION

Aryl ketones that can be used in the practice of the invention can be any aryl ketones having a removable hydrogen alpha to the carbonyl group. However, they are generally aryl ketones corresponding to the formula Ar-CO-R wherein Ar is aryl and R is a monovalent aliphatic, cycloaliphatic, or aromatic group having a removable hydrogen in the alpha-position. In such ketones the Ar group is generally an aryl group containing 6-20 carbons, most commonly a phenyl or naphthyl group which optionally bears one or more inert substituents, i.e., substituents that do not inhibit the activity of the Lewis acid in removing the removable hydrogen, such as alkyl, alkylthio, alkoxy, halo, nitro, etc. The R group is generally a saturated or unsaturated aliphatic, cycloaliphatic, or aromatic group containing 1-20 carbons, optionally bearing one or more inert substituents and sometimes joined with the Ar group to form a fused ring.

Exemplary of such ketones are phenyl alkyl ketones wherein the alkyl group is methyl, ethyl, propyl, isopropyl, butyl, isobutyl, t-butyl, pentyl, hexyl, heptyl, octyl, nonyl, decyl, dodecyl, etc.; the corresponding substituted-phenyl alkyl ketones wherein the substituents on the benzene ring may be any of the aforementioned alkyl groups and/or the corresponding alkoxy or alkylthio groups, chloro, bromo, nitro, etc.; the corresponding naphthyl or substituted-naphthyl alkyl ketones; the corresponding aryl substituted-alkyl ketones wherein the substituents on the alkyl group may be any of aforementioned inert substituents; the corresponding aryl substituted-or-unsubstituted-cyloalkyl (e.g., cyclopropyl, cyclobutyl, cyclohexyl, cyclooctyl, etc.) ketones; the corresponding aryl substituted-or-unsubstituted-alkenyl ketones wherein the unsaturation is at least one carbon removed from the carbon bearing the removable hydrogen, such as ketones in which the alkenyl group is 2-butenyl, 3-hexenyl, 4-hexenyl, 4-octenyl, etc.; the corresponding aryl substituted-or-unsubstituted-cycloalkenyl ketones; the corresponding aryl substituted-or-unsubstituted-aromatic ketones wherein said aromatic group is benzyl, phenylethyl, phenylpropyl, etc.; tetralone, etc. Among the preferred ketones are acetophenones, such as acetophenone, 4-chloroacetophenone, 4-isobutylacetophenone, 4-ethoxyacetophenone, etc., and tetralones, such as tetralone, 6-methoxytetralone, 7-bromotetralone, etc.

The Lewis acid utilized in the reaction may be any suitable Lewis acid, generally hydrogen fluoride, a trialkylaluminum, or, more preferably, a metal halide, such as boron or aluminum trifluoride, triiodide, trichloride, or tribromide, tin tetrachloride, zinc dichloride, gallium trichloride, titanium tetrachloride, diethylaluminum chloride, ethylaluminum dichloride, ethoxyaluminum dichloride, diethoxyaluminum chloride, hydroxyaluminum dichloride, dihydroxyaluminum chloride, and other such compounds wherein at least one halogen is attached to a metal atom, any remaining valences of which are usually satisfied by hydroxy, hydrocarbyl, or hydrocarbyloxy groups, generally hydroxy or alkyl or alkoxy groups containing 1-10 carbons. The preferred Lewis acids are boron trifluoride and aluminum chloride, especially aluminum chloride. This ingredient of the reaction mixture is ordinarily employed in the amount of about 0.5-1.5, preferably about 1-1.1, mols per mol of aryl ketone, although smaller or larger amounts can be employed is desired.

The cyanide ion that is reacted with the aryl ketone may be provided by any known source of cyanide ion which is free of radicals that would stabilize a cyanohydrin corresponding to the aryl ketone—a compound that is believed to be initially formed in the reaction. However, it is most commonly provided by hydrogen cyanide, a tri- or tetraalkylammonium cyanide (generally such a compound containing up to about 50 carbons) such as trimethylammonium cyanide, tributylmethylammonium cyanide, tetrabutylammonium cyanide, etc., or a metal cyanide, such as cuprous cyanide or an alkali or alkaline earth metal cyanide such as lithium, sodium, potassium, rubidium, cesium, beryllium, magnesium, calcium, strontium, or barium cyanide. The sodium, potassium, and hydrogen cyanides are generally the preferred sources of cyanide ion. The amount of cyanide ion employed is not critical, but it it usually desirable to employ about 1–5, preferably about 1–2, mols of cyanide ion per mol of aryl ketone to produce good yields of product.

The activator used in the reaction mixture is water and/or concentrated HCl—additives which appear to effect an activation of one or more of the reactants and increase yields. The particular amount of water and/or HCl employed is an activating amount, i.e., an amount insufficient to hydrolyze the Lewis acid completely, and may be provided simply by water naturally present in one or more of the other ingredients of the reaction mixture. When it is desired to employ additional water and/or HCl, the added amount is generally in the range of about 0.1–1.0 mol per mol of the aryl ketone.

Other ingredients that are suitably included in the reaction mixture are a solvent and a phase transfer catalyst. Solvents that may be employed include all solvents in which the reactants are soluble, such as aliphatic and aromatic hydrocarbons (e.g., toluene, xylenes, heptanes, and the like), chlorobenzene, nitrobenzene, etc.; but the preferred solvent is generally nitrobenzene. Particularly useful phase transfer catalysts are tetraalkylammonium halides (generally such halides containing up to about 50 carbons), preferably bromides and chlorides, such as tetrabutylammonium bromide, tributylmethylammonium chloride, etc. When employed, the catalyst is used in a catalytic amount, e.g., about 2–6% by weight of the aryl ketone; and its use sometimes seems to permit the attainment of higher yields than can be obtained in its absence.

In the practice of the invention, the ingredients of the reaction mixture may be combined in any suitable manner, preferably with the solids in finely-divided form, and heated at a suitable temperature, e.g., about 60°–120° C., preferably about 70°–90° C., to produce the desired product. Lower temperatures can be used but are less desirable because of their leading to slower reactions; higher temperatures are apt to be undesirable because of the tendency for by-products to be formed at the higher temperatures. The time required to obtain good yields varies with the temperature but is frequently in the range of about 4–10 hours.

It is sometimes preferred to combine the ingredients by prestirring the cyanide ion source, the Lewis acid, and a solvent before combining these ingredients with the aryl ketone, and it appears to be desirable to maintain the temperature of these ingredients below 60° C., e.g., at about 10°–50° C., conveniently at about 20°–30° C., until the addition of the aryl ketone has been completed.

The process is a cyanation reaction which results in the formation of an alpha-arylacrylonitrile. When an aforementioned Ar-CO-R ketone is employed as the starting material, the product corresponds to the formula Ar—C(CN)=R', wherein Ar has the same meaning as given above and R' is the divalent group obtained by removing the removable hydrogen from R.

After completion of the reaction, the product can be recovered by conventional means or, alternatively, can be subjected to further reactions without being isolated when the further reactions would not be inhibited by impurities in the crude product. It is frequently desirable to subject the alpha-arylacrylonitrile to subsequent reactions. One such reaction is a dehydrogenation of a product such as 6-methoxy-1-cyano-3,4-dihydronaphthalene to a product such a 6-methoxy-1-cyanonaphthalene—a dehydrogenation that can be accomplished, e.g., by heating the reaction mixture, preferably at reflux temperatures, in the presence of a palladium-on-carbon catalyst or by other techniques known in the art.

The invention is particularly advantageous as a one-step, commercially-acceptable process for preparing alpha-arylacrylonitriles, especially 1-cyano-3,4-dihydronaphthalenes, that can then be converted to other products.

The following examples are given to illustrate the invention and are not intended as a limitation thereof.

EXAMPLE I

An 8.47 g portion of $AlCl_3$ was added under nitrogen in a dry box to a suitable reaction vessel, followed by the addition of a 50 ml portion of dry nitrobenzene. The resulting mixture was stirred for 15 minutes, after which 5.57 g of powdered NaCN and 0.50 g of dry tetrabutylammonium bromide (TBAB) were successively added. The resulting yellow slurry was stirred for two hours. Then 10 g of distilled 6-methoxytetralone (6-MT) were added to provide a green slurry containing the 6-MT, NaCN, $AlCl_3$, and TBAB in a mol ratio of 1/2/1.1/0.03, and the reaction mixture was heated to 90° C. and maintained at that temperature for six hours. Analysis of the slurry after completion of the reaction showed it to contain 78.8% 6-MT and 19.5% 6-methoxy-1-cyano-3,4-dihydronaphthalene (6-MCDN) by GC area %.

EXAMPLE II

Example I was essentially repeated except that 0.25 g of concentrated HCl was added to the reaction mixture after the addition of the TBAB had been completed, and the reaction mixture was maintained at 90° C. for only four hours. Analysis of the final reaction mixture showed it to contain 7 area % 6-MT and 89.4 area % 6-MCDN.

EXAMPLE III

Example I was essentially repeated except that three drops of water were added to the reaction mixture after the addition of the TBAB had been completed. Analysis of the final reaction mixture showed it to contain 4.4 area % 6-MT and 90.5 area % 6-MCDN.

It is obvious that many variations can be made in the products and processes set forth above without departing from the spirit and scope of this invention.

What is claimed is:

1. A process which comprises reacting an aryl ketone having a removable hydrogen alpha to the carbonyl group with a cyanide ion source which is free of radicals that would stabilize a cyanohydrin corresponding to the aryl ketone and with a Lewis acid in the presence of an activating amount of water and/or HCl.

2. The process of claim 1 wherein an aryl ketone corresponding to the formula Ar—CO—R is reacted with the cyanide ion source and Lewis acid so as to form an alpha-arylacrylonitrile corresponding to the formula Ar—C(CN)=R', in which formulas Ar is aryl, R is a monovalent aliphatic, cycloaliphatic, or aromatic group having a removable hydrogen in the alpha-position, and R' is the divalent group obtained by removing the removable hydrogen from R.

3. The process of claim 2 wherein the aryl ketone is an acetophenone.

4. The process of claim 3 wherein the acetophenone is 4-isobutylacetophenone.

5. The process of claim 2 wherein the aryl ketone is a tetralone.

6. The process of claim 5 wherein the tetralone is 6-methoxytetralone.

7. The process of claim 1 wherein the cyanide ion source is hydrogen cyanide, a tri- or tetraalkylammonium cyanide, or a metal cyanide.

8. The process of claim 7 wherein the cyanide ion source is an alkali metal cyanide.

9. The process of claim 8 wherein the alkali metal cyanide is sodium cyanide.

10. The process of claim 1 wherein the Lewis acid is a metal halide.

11. The process of claim 10 wherein the metal halide is aluminum chloride.

12. The process of claim 1 wherein the reaction is conducted in the presence of a catalytic amount of a phase transfer catalyst.

13. The process of claim 12 wherein the phase transfer catalyst is tetrabutylammonium bromide.

14. The process of claim 1 wherein the reaction is conducted in a solvent.

15. The process of claim 18 wherein the solvent is nitrobenzene.

16. The process of claim 1 wherein the reaction is conducted in the presence of about 0.1–1.0 mol of added water and/or HCl per mol of aryl ketone.

17. The process of claim 1 wherein the reaction is conducted at a temperature of about 60°–120° C.

18. A process which comprises reacting a tetralone having a removable hydrogen alpha to the carbonyl group with sodium cyanide and aluminum chloride at a temperature of about 60°–120° C. and in the presence of about 0.1–1.0 mol of added water and/or HCl per mol of tetralone so as to form a 1-cyano-3,4-dihydronaphthalene.

19. The process of claim 18 wherein the tetralone is 6-methoxyteralone and the product is 6-methoxy-1-cyano-3,4-dihydronaphthalene.

* * * * *